United States Patent [19]

Pâques et al.

[11] Patent Number: 4,621,631
[45] Date of Patent: Nov. 11, 1986

[54] PROCESS FOR THE PRODUCTION OF A BONDED COLLAGEN FIBER SHEET

[75] Inventors: Eric P. Pâques, Marburg; Peter Fuhge, Lahntal, both of Fed. Rep. of Germany

[73] Assignee: Behringwerke Aktiengesellschaft, Fed. Rep. of Germany

[21] Appl. No.: 564,917

[22] Filed: Dec. 23, 1983

[30] Foreign Application Priority Data

Dec. 27, 1982 [DE] Fed. Rep. of Germany ....... 3248188

[51] Int. Cl.[4] .............................................. A61F 13/00
[52] U.S. Cl. ................................ 128/156; 128/334 R; 128/335.5; 128/DIG. 8; 435/273; 514/801; 530/356
[58] Field of Search .............. 128/334, 335.5, DIG. 8, 128/156; 260/123.7; 424/36, 28, DIG. 13; 264/330; 435/273; 604/368; 514/801

[56] References Cited

U.S. PATENT DOCUMENTS

| | | | |
|---|---|---|---|
| 2,838,363 | 6/1958 | Veis et al. | 260/123.7 |
| 3,742,955 | 7/1973 | Battista et al. | 128/334 |
| 4,066,083 | 1/1978 | Ries | 435/273 |
| 4,140,537 | 2/1979 | Luck et al. | 260/123.7 |
| 4,320,201 | 3/1982 | Berg et al. | 435/265 |
| 4,331,766 | 5/1982 | Becker et al. | 435/273 |
| 4,389,487 | 6/1983 | Ries | 435/273 |
| 4,404,134 | 9/1983 | Becker et al. | 435/273 |

FOREIGN PATENT DOCUMENTS

| | | |
|---|---|---|
| 696434 | 10/1964 | Canada . |
| 2734503 | 2/1979 | Fed. Rep. of Germany . |
| 1444812 | 8/1976 | United Kingdom . |

*Primary Examiner*—Veronica P. Hoke
*Attorney, Agent, or Firm*—Finnegan, Henderson, Farabow Garrett & Dunner

[57] ABSTRACT

A process for the production of an unnative and biologically active bonded collagen fiber sheet from human placentae is described, in which process collagen-containing material from placentae is treated with a neutral salt solution, a solution of citric acid and with pepsin. The degraded collagen material obtained in this manner is, where appropriate, treated with a crosslinking agent. The collagen material produced in this manner is used for producing bonded collagen fiber sheets which can be used, for example, as covering for wounds.

6 Claims, No Drawings

PROCESS FOR THE PRODUCTION OF A BONDED COLLAGEN FIBER SHEET

The invention relates to a process for the production of an unnative and biologically active bonded collagen fiber sheet from human placentae.

Collagen is a fibrous protein which is found principally in the skin, tendons, bones and connective tissue of humans and animals. Collagen fibers in the walls of vessels bring about the adhesion and aggregation of platelets and thus have an effect on hemostasis.

The use of collagenous materials for accelerating the healing of wounds is known. Collagen leads to a marked increase in wound stability and intensifies the growth of fibroblasts.

The production of collagen preparations from animal or human starting material has already been described. A process for obtaining biologically active collagen from human placenta, using a number of washing steps and degradation by pepsin, is described in European Patent Application No. 0,023,607. In addition, processes for the production of bonded collagen fiber sheets are also described in European Patent Application No. 0,042,253, in U.S. Pat. Nos. 3,471,598 and 3,823,212, German Patent No. 2,943,520 and German Offenlegungsschriften Nos. 2,734,503 and 2,348,685. However, the products thus produced are not entirely satisfactory on therapeutic use since they do not have, at one and the same time, all the desired physical and biological properties.

It has been found, surprisingly, that, by modifying the process of European Offenlegungsschrift No. 0,023,607 and treating the material containing collagen with a solution of citric acid, an intensified platelet-aggregating effect and a decrease in contamination with hepatitis virus B antigen are achieved. At the same time, surprisingly, it is possible, using the collagen solution produced in this manner, to produce bonded collagen fiber sheets having optimal biological and physical properties.

Thus the invention relates to a process for the production of a bonded collagen fiber sheet by treating collagen-containing material with neutral salt solutions and a solution of pepsin, precipitating the collagen with a neutral salt, and treating it with a crosslinking agent, which comprises treating the collagen-containing material with citric acid.

In particular, the invention relates to a process for the production of bonded collagen fiber sheets by treating collagen-containing material with a neutral salt solution, a solution of citric acid, a solution of pepsin and, where appropriate, an ion exchanger, and precipitating the collagen with a neutral salt, taking up the residue in a weakly buffered solution, dialyzing against water, and treating the precipitate with a crosslinking agent.

An example of a preferred process entails washing placentae, which have been comminuted and washed free of blood, with a 0.5–4 molar neutral salt solution, preferably a 2 mol/l sodium chloride solution, and a 0.5–2 molar citric acid solution at pH 1–4, preferably a 1 mol/l citric acid solution at pH 2, and degrading them with pepsin. Where appropriate, the resulting solution can be treated with, for example, an ion exchanger resin to remove low and high molecular weight contaminants. The process also entails taking up and dissolving, with sodium chloride in a weakly buffered solution at pH 4–9, preferably pH 4–6, the precipitate from a precipitation, dialyzing against water, preferably for 16 hours, suspending the resulting precipitate in aqueous solution, preferably at pH 8, treating the solution with a crosslinking agent, preferably formaldehyde, at a concentration of 0.01–0.1 g/l, preferably 0.05 g/l, at a temperature of 4°–37° C., preferably 25° C., for 0.5 to 24 hours, preferably 4 hours, and drying, preferably freeze-drying.

In a particularly preferred embodiment, the process is such that human placentae, which have been comminuted and washed free of blood, are treated with a weakly buffered salt solution at pH 7–9 and a concentration of 0.5–4 mol/l, preferably with 40–50 liters of a weakly buffered 2 mol/l NaCl solution per kg of placental material, and the precipitate is separated off, washed with, preferably, 40–50 liters of water per kg of placental material, treated with 4–50 liters of a 0.5–2 mol/l solution of citric acid at pH 2, preferably 4 liters of a 1 mol/l solution of citric acid, per kg of placental material, for 0.5 to 24 hours, preferably 2 hours, at a temperature of 2°–25° C., preferably 4° C., and the precipitate which has been separated off is washed with water, taken up in an aqueous solution of an acid having a pK of 3–5, preferably with 0.1 mol/l acetic acid, the pH is adjusted to 2, preferably with hydrochloric acid, the solution is treated with pepsin for 15 to 30 hours, preferably 24 hours, at 4°–30° C., preferably 25° C., the pepsin treatment is repeated, a silicate-containing adsorbing agent, for example Dicalite (R) speed plus, is added to the solution where appropriate, and the supernatant is separated off, this solution is adjusted to a pH of 7–11 by addition of a buffer, preferably tris/hydrochloric acid, and, where appropriate, an anion exchanger is added and separated off, the solution is adjusted to a pH of 2–3 by the addition of an acid, for example hydrochloric acid or acetic acid, the collagen is precipitated by increasing the ionic strength, preferably by addition of neutral salt to a concentration of 0.6–1.3 mol/l, the precipitate which has been separated off is dissolved in a weakly buffered solution at pH 4–9, preferably pH 5, the collagen solution obtained in this manner is dialyzed against water, preferably for 16 hours at 4° C., whereupon collagen fibrils separate out, the fibrils are homogenized, and the suspension is treated, preferably at pH 8 for 0.5 to 24 hours, preferably 4 hours, with formaldehyde at a final concentration of 0.01–0.1 g/l, preferably 0.05 g/l, at 4°–37° C., preferably 25°–37° C., and the suspension is brought to dryness, preferably by freezing at −60° C. to −5° C., preferably −40° C., and freeze-drying.

It is possible to sterilize the bonded collagen fiber sheets by, preferably, γ-radiation.

A bonded collagen fiber sheet produced in this manner is distinguished by lack of odor, a white color, high tear resistance, good plasticity, elasticity and hydrophilicity, and by a tendency to induce platelet aggregation.

The tanning with formalin prevents the danger of transmission of non-A,non-B hepatitis viruses (E. Tabor, R. J. Genty: J. of Infect. Dis. 142 (5), 767–770, 1980).

In spite of the treatment with formalin and sterilization with γ-rays, the bonded fiber sheet produced according to the invention has a strong platelet-aggregating effect, which has not been found with bonded collagen fiber sheets produced according to the state of the art.

Thus, a bonded fiber sheet produced in the manner described is particularly suitable for the production of coverings for wounds, which can be used not only for stabilizing wounds and intensifying the formation of fibroblasts, but can also be used for hemostasis, including, specifically, for patients having a particular tendency to bleed (hemophilia), for example after tooth extraction.

The invention is to be illustrated in detail by the examples which follow.

EXAMPLE 1

5 kg of placental residue which is obtained by extracting placentae, which have been washed free of blood and comminuted, with isotonic saline and separating off the extract, was again comminuted, centrifuged down and extracted with 250 liters of 0.05 mol/l tris/HCl buffer, pH 7.4, containing 2 mol/l of NaCl. The suspension was decanted, and the precipitate was washed three times with 250 liters of water at 4° C. and the suspension was decanted. The precipitate was then suspended in 250 liters of 1 mol/l citric acid and, after 1 hour, the supernatant was decanted off. The precipitate was finely divided using a homogenizer, then washed with 20 liters of water at 4° C. and centrifuged. The precipitate was taken up in 20 liters of 0.1 mol/l acetic acid and, with stirring, adjusted to a pH of 2 with 1 N hydrochloric acid. 2 g of pepsin (110 Anson units per mg) were added and the mixture was stirred at a temperature of 25° C. for 24 hours. Fresh pepsin was added to this solution, and stirring was continued under the same conditions. After adding 40 g/l of Dicalite ®, the mixture was homogenized and centrifuged down. The supernatant was adjusted to pH 8.0 by the addition of tris, and stirred with 50 g/l of Dowex ® 2×8 for one hour, centrifuged down and the pH was adjusted to 2. The solution was adjusted to a concentration of 0.2 mol/l with solid NaCl. After stirring for 2 hours, the suspension was centrifuged and the supernatant was discarded. The precipitate was taken up in 10 liters of water, the pH was adjusted to 5 with acetic acid, and the solution was dialyzed against water, collagen precipitating out in the form of odorless white fibrils.

EXAMPLE 2

As Example 1, the placental residue being extracted with 25 liters of 0.5 mol/l citric acid for 18 hours in place of the citric acid treatment indicated there.

EXAMPLE 3

As Examples 1 and 2, a 2 mol/l sodium chloride solution being used for the first extraction in place of tris buffer.

EXAMPLE 4

A collagen suspension according to Example 1, 2 or 3 and a collagen suspension produced according to European Offenlegungsschrift No. 0,023,607 were tested at the same concentration in a Born aggregometer with recorder (supplied by Braun, Melsungen, F. R. G.). For this purpose, 1 ml of citrated plasma rich in platelets was placed in the cell, and the photometer and recorder were set at 0% transmission. Equilibration at a temperature of 37° C. was awaited, with stirring. Then the particular collagen suspension was added and the increase in transmission caused by platelet aggregation was measured. The activity of the collagen obtained according to Example 1, 2 or 3 was found to be 10 times higher than the collagen of the state of the art.

Reference: Born G. W. R., J. Physiol. (London) 162, 67 (1962)

EXAMPLE 5

The process according to the invention was carried out with the addition of sufficient amounts of HBsAg to test the suitability of this process in respect of removing HBsAg.

| Step | HBsAg (µg) amount added | amount remaining | Depletion factor |
|---|---|---|---|
| NaCl wash ↓ | 9,000 | | |
| Supernatant of the 2nd water wash | — | 82 | 110 |
| Citric acid wash ↓ | 900 | — | |
| Supernatant of the 3rd water wash | — | 7 | 129 |
| Pepsin degradation ↓ | 1,000 | — | |
| Collagen solution | — | 58 | 17 |

A depletion factor of about 240,000 was found.

EXAMPLE 6

300 ml portions of a suspension containing 8–12 g/l of collagen fibrils, pH 5, were homogenized, the pH was adjusted to 8, and they were treated with formaldehyde at a concentration of 0.05 g/l at 250° C. for 4 hours. The suspensions were frozen at −40° C. and freeze-dried to produce bonded fiber sheets.

EXAMPLE 7

Bonded collagen fiber sheets were produced as in Example 6. However, the crosslinking with formalin was carried out at various pH values between 4 and 10. The bonded collagen fiber sheets were tested for their tear resistance.

Tanning pH Tear resistance (g)

| Tanning pH | Tear resistance (g) |
|---|---|
| 4 | 51 |
| 6 | 67 |
| 7 | 99 |
| 8 | 166 |
| 10 | 120 |

EXAMPLE 8

Bonded collagen fiber sheet obtained according to the invention and two commercially available conventional bonded collagen fiber sheets were tested as described in Example 4, the collagen solution being replaced by the same amount of bonded collagen fiber sheet. Only the bonded fiber sheet produced by the process according to the invention initiated platelet aggregation.

EXAMPLE 9

Bonded collagen fiber sheets were produced as in Example 5. However, the collagen which had been precipitated with sodium chloride was dissolved in a weakly buffered solution at pH 4.0–9.0 and dialyzed against water. The bonded collagen fiber sheets produced were tested for their physical and biological properties. The best results were observed with the solution of collagen dissolved at pH 5.0 (see table).

| pH | Rate of water uptake (sec) | Amount of water taken up (g) | Tear resistance (g) | Elasticity |
|---|---|---|---|---|
| 4.0 | 25.0 | 1.1 | <30 | 23 |
| 5.0 | 1.8 | 1.9 | 216 | 5.5 |
| 6.0 | 1.9 | 1.8 | 110 | 7.5 |
| 7.0 | 2.3 | 0.94 | <30 | 17.7 |
| 8.0 | 11.5 | 1.0 | <30 | >180 |
| 9.0 | 30.0 | 0.92 | <30 | >180 |

We claim:

1. A process for the production of a bonded collagen fiber sheet by sequentially treating collagen containing material, which have been comminuted and washed free of blood, with a 0.5-4 molar neutral salt solution, a 0.5-2 molar citric acid solution at pH 1-4, a pepsin solution, and, where appropriate, with an ion exchanger resin to remove low and high molecular weight contaminants, precipitating the collagen with sodium chloride, dissolving the precipitate in a weakly buffered solution at pH 4-6 to form a collagen solution, dialyzing the collagen solution against water so as to precipitate the collagen fibrils, suspending the collagen fibrils and drying the collagen.

2. The process as claimed in claim 1 further comprising treating the suspended collagen fibrils with a crosslinking agent at a concentration of 0.01-0.1 g/l at a temperature of 4°-37° C. for 0.5-24 hours and drying the crosslinked collagen.

3. The process of claim 2 wherein the crosslinking agent is formaldehyde.

4. The processes as claimed in claim 1, 3 or 2 wherein the collagen containing material is placentae.

5. A bonded collagen fiber sheet produced in accordance with the processes of claim 3 or 2.

6. The application of a bonded fiber sheet produced in accordance with the process of claim 3 or 2 as a covering for wounds.

* * * * *